US00PP25387P3

(12) United States Plant Patent
Nussbaumer

(10) Patent No.: US PP25,387 P3
(45) Date of Patent: Mar. 31, 2015

(54) APPLE TREE NAMED 'STARK GUGGER'

(50) Latin Name: *Malus domestica*
Varietal Denomination: Stark Gugger

(71) Applicant: Griba Baumschulgenossenschaft Landw.Gesellschaft, Terlan (IT)

(72) Inventor: Werner Nussbaumer, Leifers (IT)

(73) Assignee: Griba Baumschulgenossenschaft Landw. Gesellschaft, Terlan (IT)

( * ) Notice: Subject to any disclaimer, the term of this patent is extended or adjusted under 35 U.S.C. 154(b) by 111 days.

(21) Appl. No.: 13/815,149

(22) Filed: Feb. 4, 2013

(65) Prior Publication Data

US 2014/0223622 P1 Aug. 7, 2014

(51) Int. Cl.
*A01H 5/00* (2006.01)

(52) U.S. Cl.
USPC ..... Plt./171

(58) Field of Classification Search
USPC ..... Plt./171
See application file for complete search history.

(56) References Cited

PUBLICATIONS

UPOV-PLUTO: Plant Variety Database 20140721; cultivar name 'Stark Gugger'.*
Community Plant Variety Office (CPVO) application for 'Stark Gugger', Jul. 25, 2011, 16 pages.
"Red Velox, colore precoce, intenso e uniforme", *Rivista di Frutticoltura e di ortofloricoltura*, Anno LXXIV-N.11, Nov. 2012, 2 pages.

* cited by examiner

*Primary Examiner* — Susan McCormick Ewoldt
(74) *Attorney, Agent, or Firm* — Myers Bigel Sibley & Sajovec, PA

(57) ABSTRACT

*Malus domestica* Borkh 'Stark Gugger' variety is distinguished from the 'Starking Delicious' variety and other Red Delicious varieties by the a unique combination of characteristics including purple red fruits with solid flush coloration on 100% of the surface, a fruit shape that is long truncated-conical with pronounced crowning at distal end, fruit coloration that starts 10 days earlier than other Red Delicious varieties; an anticipation of fruit maturation of 5-7 days compared to other Red Delicious variety and a growth habit that is standard (not spur) 20% stronger than other Red Delicious standard.

10 Drawing Sheets

Latin name of the genus and species: The Latin name of the genus and species of the plant variety disclosed herein is *Malus domestica* Borkh.

Variety denomination: The inventive cultivar of *Malus domestica* Borkh disclosed herein has been given the varietal denomination 'Stark Gugger'.

BACKGROUND OF THE INVENTION

The present invention relates to a new and distinct Red Delicious variety of apple tree named 'Stark Gugger', which was discovered as a sport limb mutation on a 'Starking Delicious' plant in a cultivated field in Bressanone area, Bolzano province. The mutated branch was easily identified and noticed because of the anticipated and strong red-purple and solid-flush coloration of the fruits compared to the other fruits on the plant (FIG. 1).

The progeny was first asexually propagated in Spring 2005 and 10 trees were initially grown. The first observed fruiting of the propagated trees occurred in the 2006 season and confirmed the intensity of the fruit red-purple coloration and the stability of the mutation. Anticipation of 5-7 days in maturation time also has been observed compared to other Stark Delicious clones.

In the following years, many other trees were asexually propagated, planted and evaluated in other locations in Bolzano province and Verona province. All the trees of 'Stark Gugger' have been observed to remain true to type over successive asexually propagated generations and maintain the intensity of colour and the anticipation in fruit maturation.

SUMMARY OF THE INVENTION

The 'Stark Gugger' variety is distinguished from the 'Starking Delicious' variety and other Red Delicious varieties by the following unique combination of characteristics: Purple red fruits with solid flush coloration on 100% of surface; a fruit shape that is long truncated-conical with pronounced crowning at distal end; a fruit coloration that starts 10 days earlier than other Red Delicious varieties; an anticipation of fruit maturation of 5-7 days compared to other Red Delicious variety; and a growth habit that is standard (not spur) 20% stronger than other Red Delicious standard.

Compared to 'Sandidge' (U.S. Plant Pat. No. 6,190), 'Stark Gugger' has standard growth habit (not spur), solid flush red purple coloration (not striped), and 7 days earlier maturation time.

Compared to 'Jeromine' (PBR grant number 6599), 'Stark Gugger' has 20% higher standard growth on M9 rootstocks, and 5 to 7 days earlier maturation time.

Compared to 'Early Red One' (U.S. Plant Pat. No. 3,556), 'Stark Gugger' has 20% higher standard growth on M9 rootstocks, 5 days earlier maturation time and solid flush red purple coloration (not striped).

Asexual reproduction of this new variety by grafting and budding onto rootstock shows that the foregoing and all other characteristics and distinctions come true to form and are established and transmitted through succeeding propagations.

BRIEF DESCRIPTION OF THE DRAWINGS

The colours of these illustrations may vary with lighting conditions and, therefore, colour characteristics of this new variety should be determined with reference to the observations described herein, rather than from these illustrations alone.

FIG. 7, profile; FIG. 8, calix eye; FIG. 9, stalk cavity.

DETAILED BOTANICAL DESCRIPTION

The following detailed description of the 'Stark Gugger' variety is based on observations made during the 2012 growing season in a high density 'Stark Gugger' planting field in Bressanone area, Bolzano Province (Italy).

Certain characteristics of this variety may change with changing environmental conditions (e.g., light, temperature, moisture), nutrient availability, and/or other factors. Quantified measurements are expressed as an average of measurements taken from a number of individual plants of the new variety. The measurements of any individual plant, or any group of plants, of the new variety may vary from the stated average. Colour descriptions and other terminology are used in accordance with their ordinary dictionary descriptions, unless the context clearly indicates otherwise. Colour designations are made with reference to The Royal Horticultural Society (R.H.S.) Colour Chart.

Figure 1:
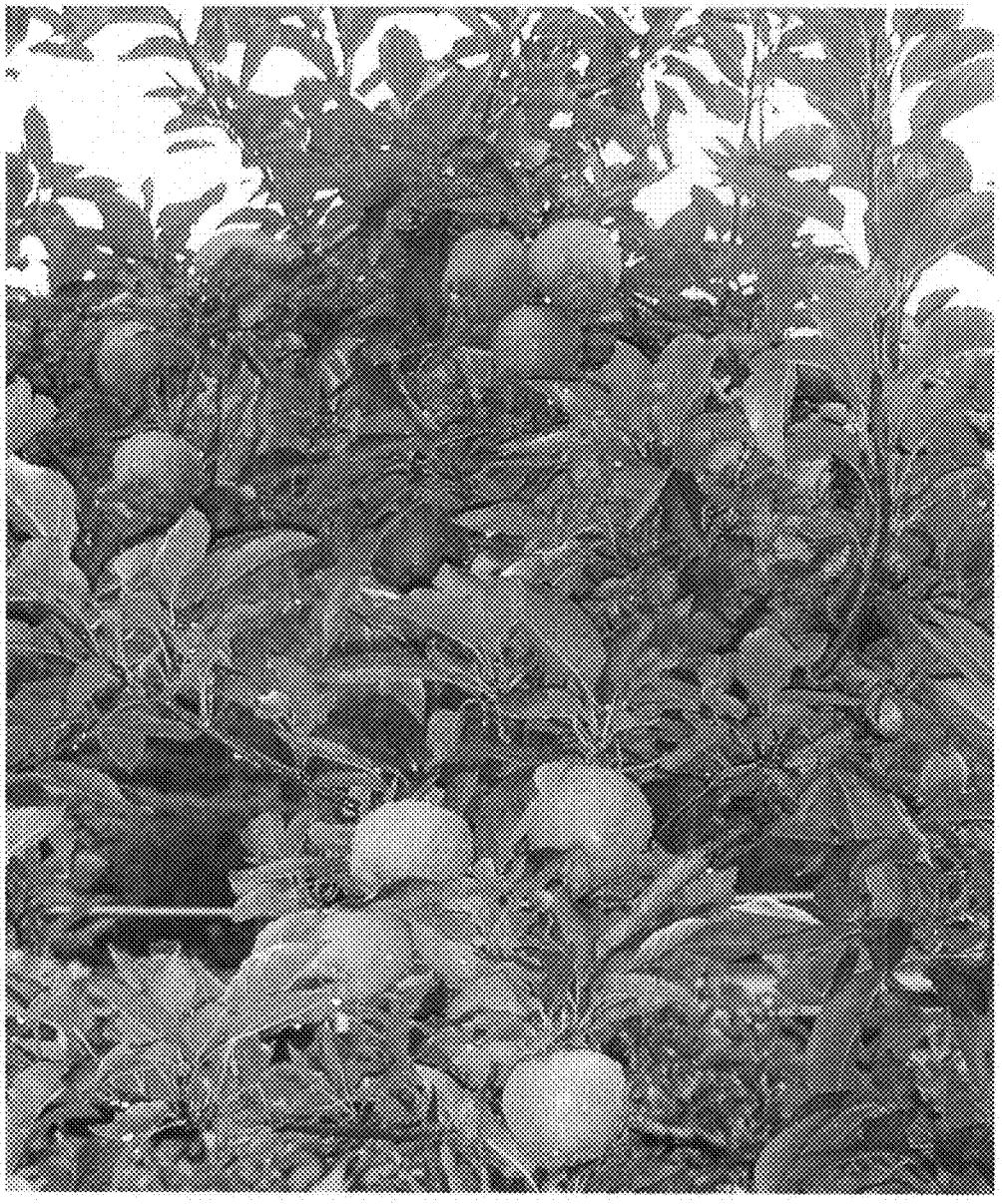
FIG. 1 illustrates the 'Starking Delicious' mother plant (age 14 years) where the 'Stark Gugger' mutation has been identified. A branch on the top of the plant presented fully coloured dark red apples and earlier coloration compared to the lower branches of original 'Starking Delicious'.

Parentage: 'Stark Gugger' variety originated by a sport on the top part of a 'Starking Delicious' standard plant, identified in 2004 in a cultivated field in Bressanone area, Bolzano province. The mutated branch was easily identified and noticed because of the anticipated and strong red purple coloration of the fruits compared to the other 'Starking Delicious' fruits (FIG. 1). At ripening time, the 'Starking Delicious' fruits on the non-mutated parent plant appeared striped red over-colored on green yellow ground color. The striped red over-color covered 50% of the fruit surface of light red color (Red RHS 53B), while the apples on the mutated branch that originated 'Stark Gugger' were dark red colored (Purple-red RHS N77A) without stripes.

Figure 2:
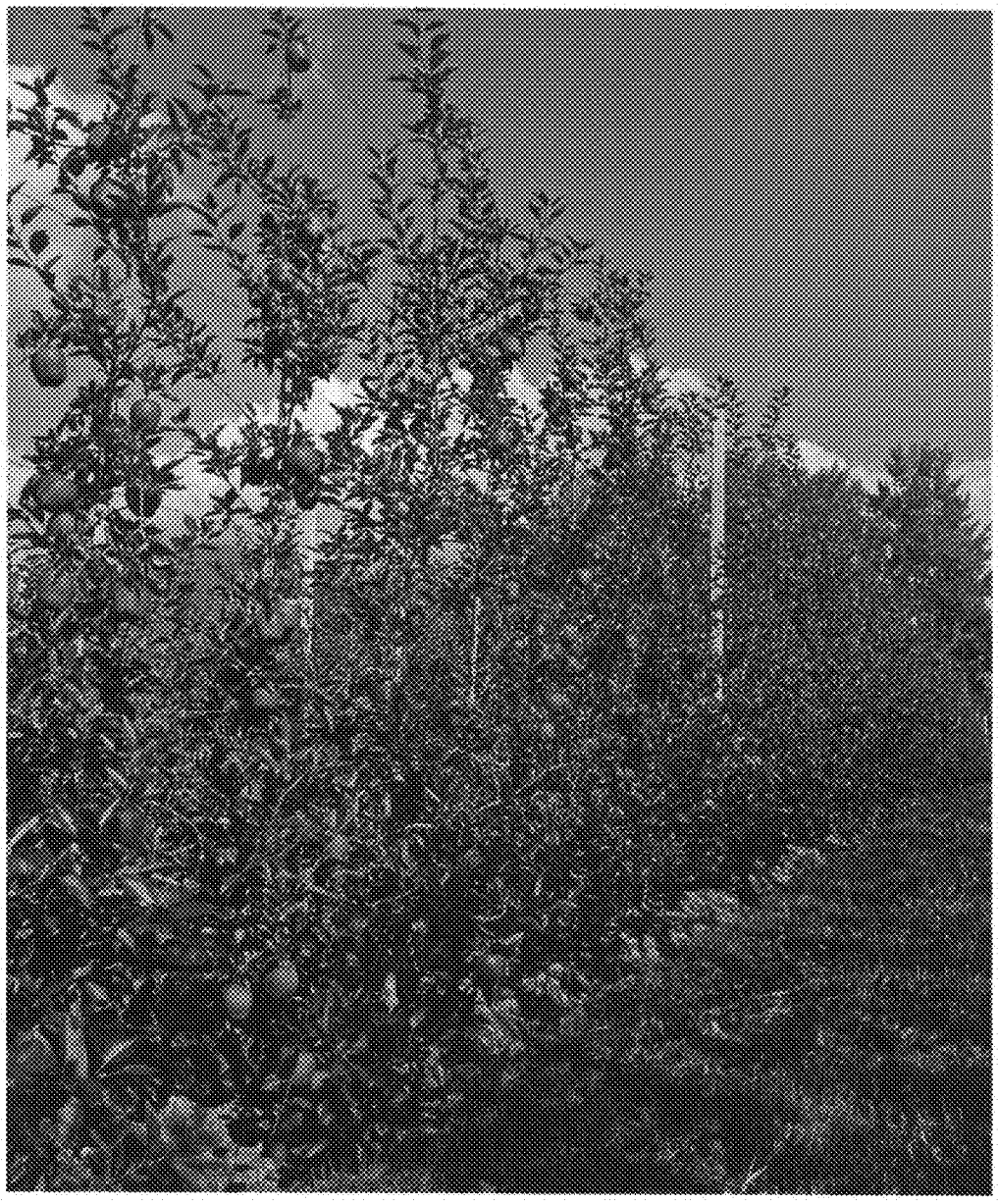
FIG. 2 and FIG. 3 illustrate 4 year old 'Stark Gugger' trees of second generation at harvesting time. The plants vegetatively propagated on M9 rootstocks, present a growing habit of type standard with medium growth and spreading branches, predominance of bearing on shoots.
Figure 3:
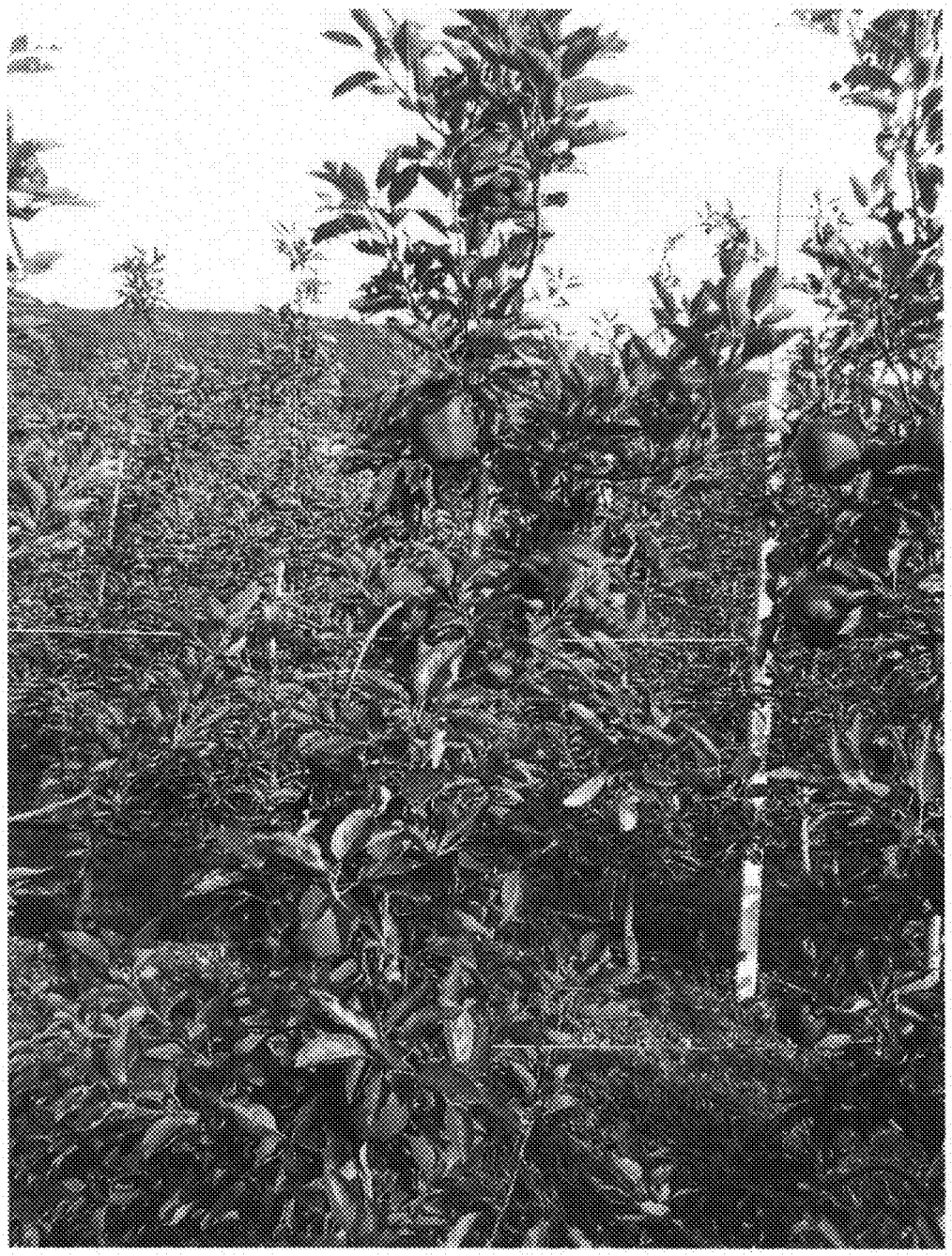

Tree: The trees here described are four-year-old trees grown on M9 rootstock deriving from the second generation vegetatively propagated 'Stark Gugger' sport. (FIG. 2 and FIG. 3).

Vigour and overall shape: 'Stark Gugger' trees on M9 rootstock show a standard ramified (non spur) growth habit with medium vigour, 20% stronger than Red Delicious 'Jeromine' and other Red Delicious standard clones.

*Height.*—3.30 m.

*Width.*—1.20 m.

Trunk: Medium Stocky; diameter, 45 mm at 200 mm above the graft union; bark texture, smooth; bark colour, Brown RHS N200-C.

Primary branches: Basal branches emerge at 700 mm from the soil with an angle of about 60 to 90 degrees. Three year old branches: length, 600-700 mm; diameter measured at the base, 27 mm; crotch angle, 70 to 90 degree; colour Greyed-Red RHS 182C.

*One-year old branches.*—Length, 340 mm; tichness, 7.8 mm; internode length, 32 mm; colour at middle of July, Greyed-Purple RHS 183D; pubescence, medium-high White RHS N155A; number of lenticels per square centimetre, 8; lenticel shape, elongated-round; lenticels colour Grey RHS 198C.

Bearing: Annual, principally on flower-buds on shoots, sometimes on spurs; very low or not subjected to alternate bearing.

Hardiness: European hardiness Zone 6, comparable to other Red Delicious varieties.

Drought, disease and insect resistance: Susceptibility to classical apple disease comparable to other Red Delicious varieties.

Figure 5:
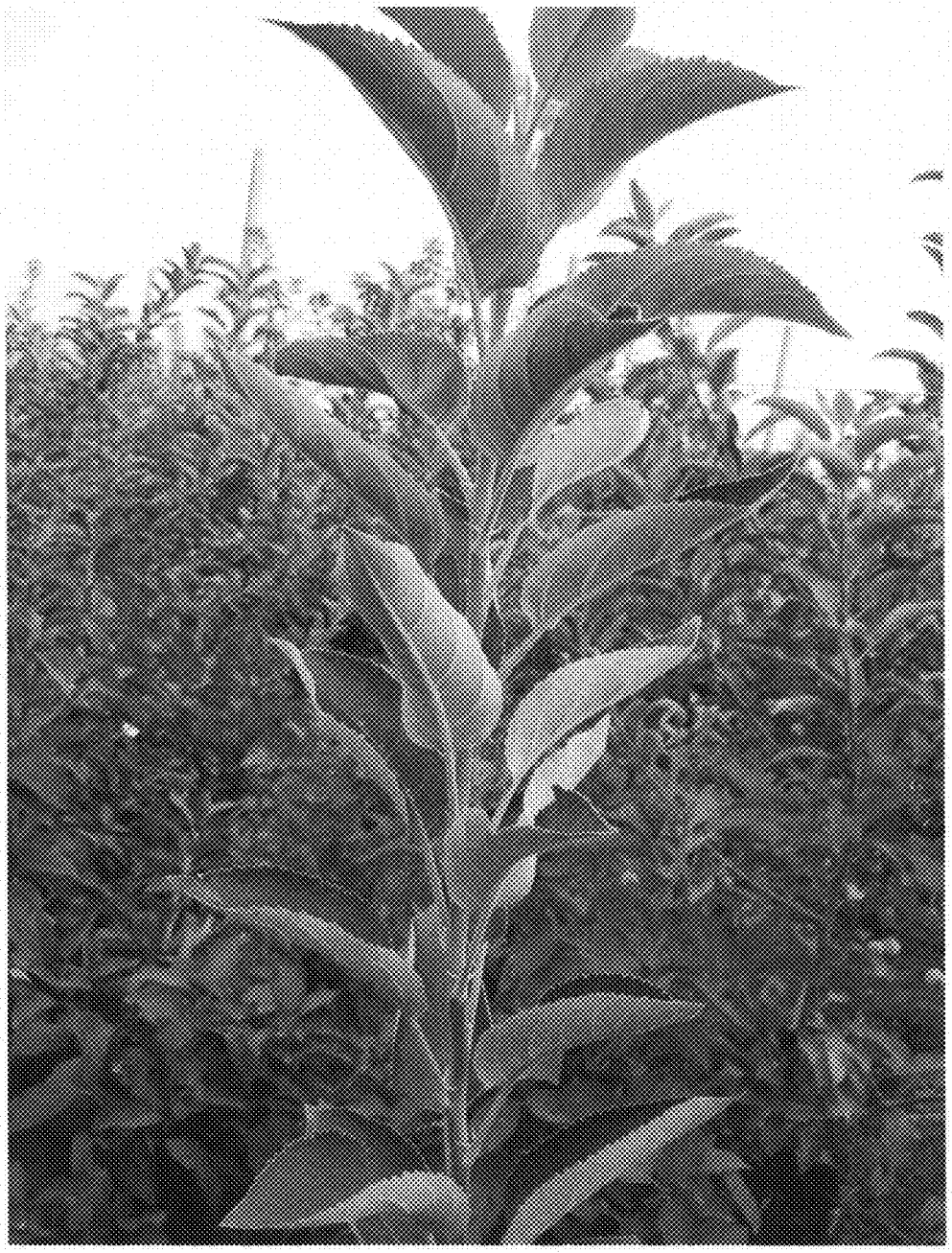
FIG. 5 illustrates 'Stark Gugger' actively growing shoot at middle of July, the bark of the shoot and the basal part of leaf are greyed-purple coloured.
Figure 6:
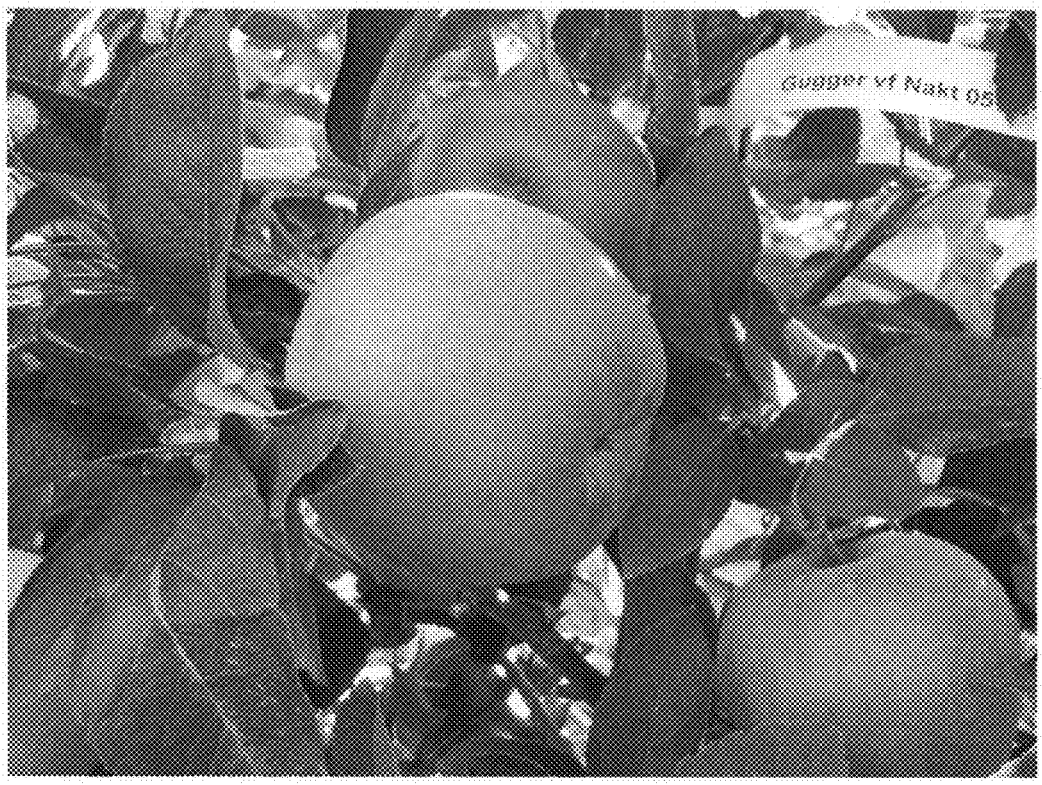
FIG. 6 illustrates the early red purple coloration of 'Stark Gugger' apples already at middle of July.

Leaves: Shape, elliptic; length, medium-long 104 mm; width, 4.9 mm; length/width ratio, 2.12; blade margins, bi-crenate; apex, acuminate; base shape, truncate; colour of upper surface, Green RHS 133A; colour of lower surface, Green RHS 143A; pubescence on lower surface, light-medium; pubescence colour, White RHS N155A; leaf attitude in relation to shoot, upward to outward (FIG. 5).

*Petiole.*—Length, medium 36 mm; thickness, medium 2.7 mm, colour, Yellow-Green RHS 147C tinged on lower surface on Greyed-Purple RHS 185C; petiole pubescence, light, colour White RHS N155A.

*Stipules.*—Quantity, 2 opposite; thin; length 7 mm; colour, Yellow-Green RHS 147B.

Flowers. Flower buds (unopened flower): number per cluster, 5 to 6; length, 15 mm; diameter, 10 mm; shape, round-conical; colour, Red-Purple RHS 61C. Open flower: size, medium-large; diameter, 43 mm; pollination requirement varieties, 'Gala' 'Golden Delicious' 'Granny Smith' 'Idared' 'Summerred' and other varieties flowering in the same period except for Red Delicious group.

Petals: Number per flower, 5; relative position of petal margins, slightly overlapping; shape, ovoid-elliptic; length, 20 mm; width, 14 mm; apex, rounded; base, conical pointed; margin, smooth; colour of upper surface, White RHS NN155D; colour of lower surface, White RHS N155D.

Pistil: Size, medium 16 mm long; stigma colour, Yellow-Green RHS 145D; styles quantity, 5; style colour, Yellow-Green RHS 145B; ovary colour, Green RHS 143A.

Anthers: Quantity 20 to 25 per flower; size, 2.3 mm; presence of pollen; colour of pollen, Yellow RHS 4B.

Sepals: Quantity, 5; shape, conical pointed; colour, Green RHS 143A.

Pedicel: Length 20 mm; diameter, 2 mm; colour, Green RHS 143A.

Bloom season: In 2012 at Bressanone area in Bolzano Province, Italy, blooming began the 10$^{th}$ of April; full bloom was the 16$^{th}$ of April; finishing on the 20$^{th}$ of April.

Figure 4:
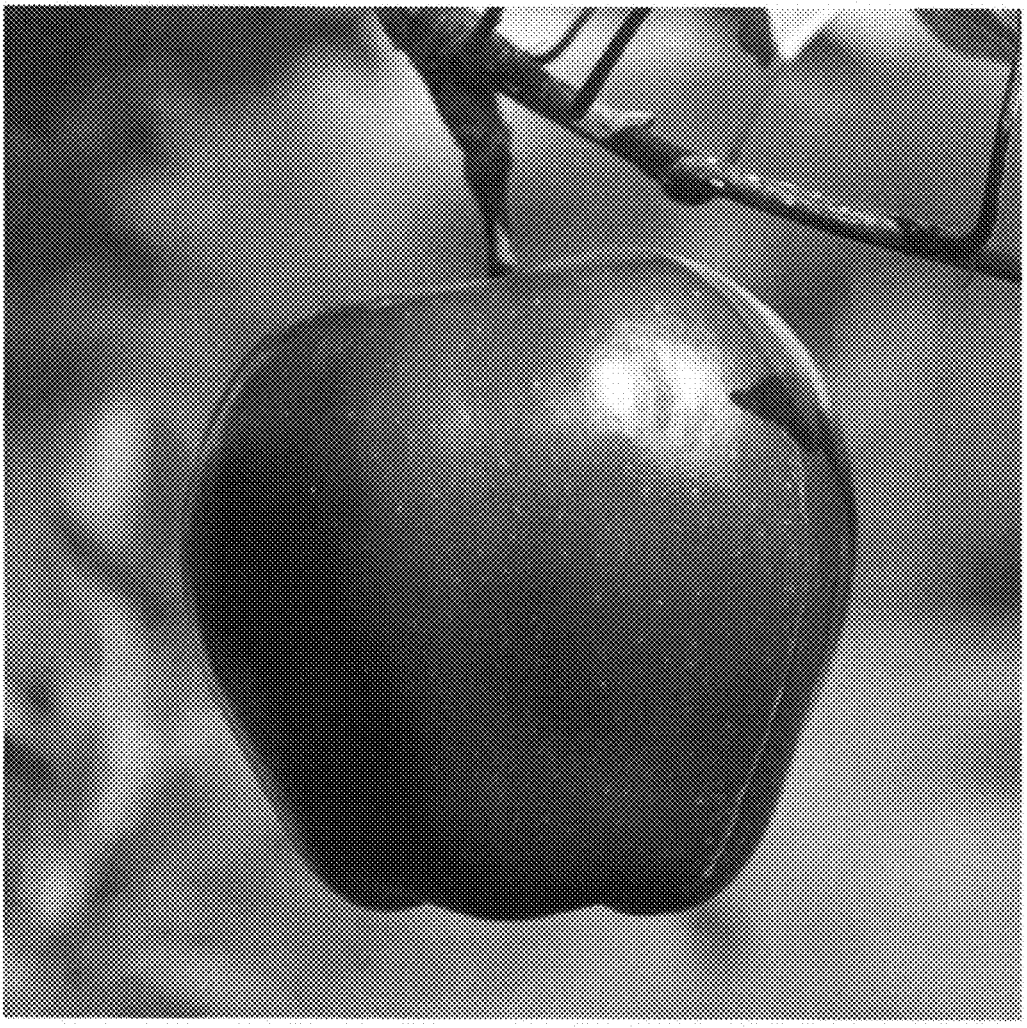
FIG. 4 illustrates a typical 'Stark Gugger' apple at picking time with solid flush dark red colour and long truncated conical shape.
Figure 7:
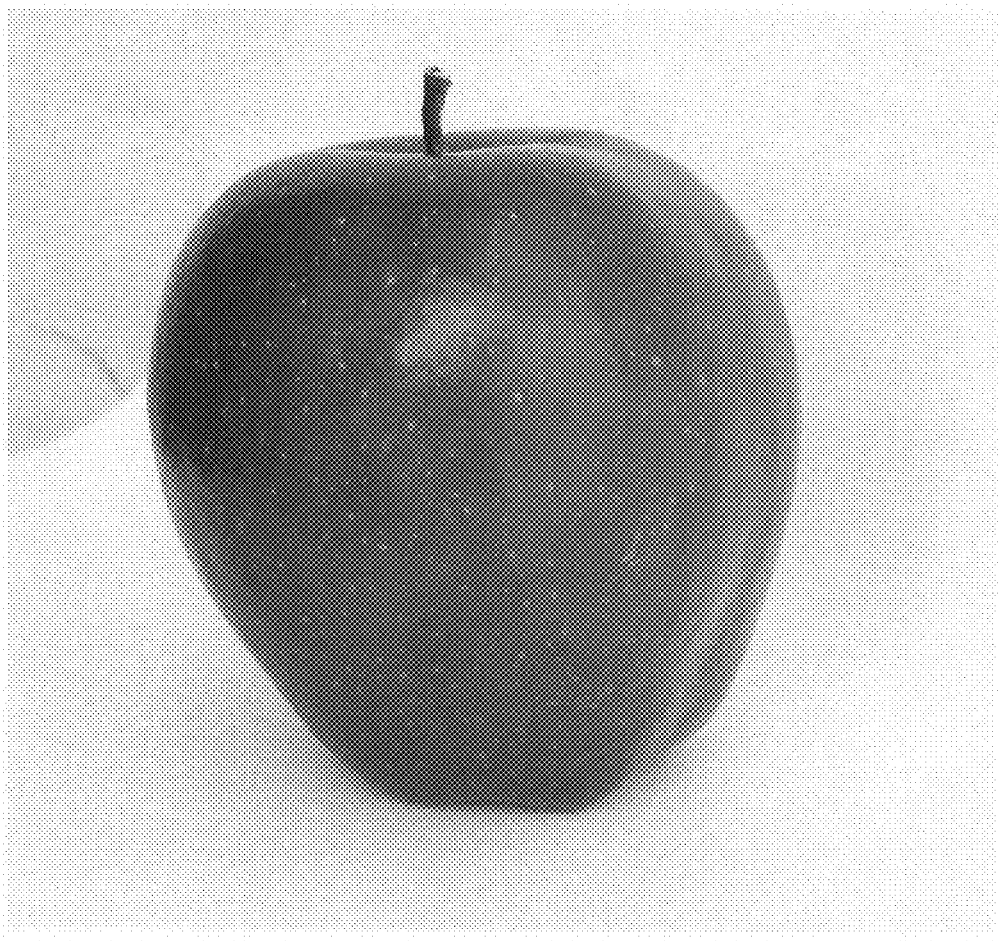
FIGS. 7-9 illustrate a 'Stark Gugger' apple after harvesting (wiped from the wax with a dry rag).
Figure 8:
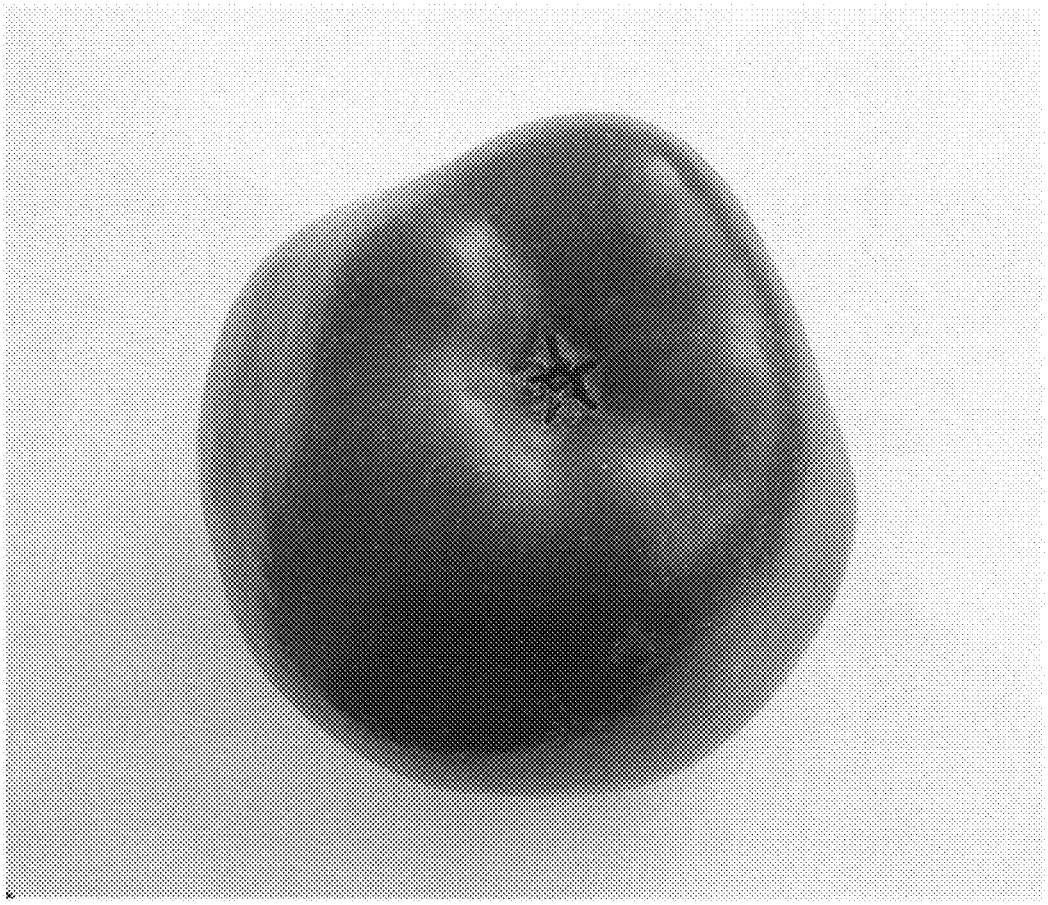
Figure 9:
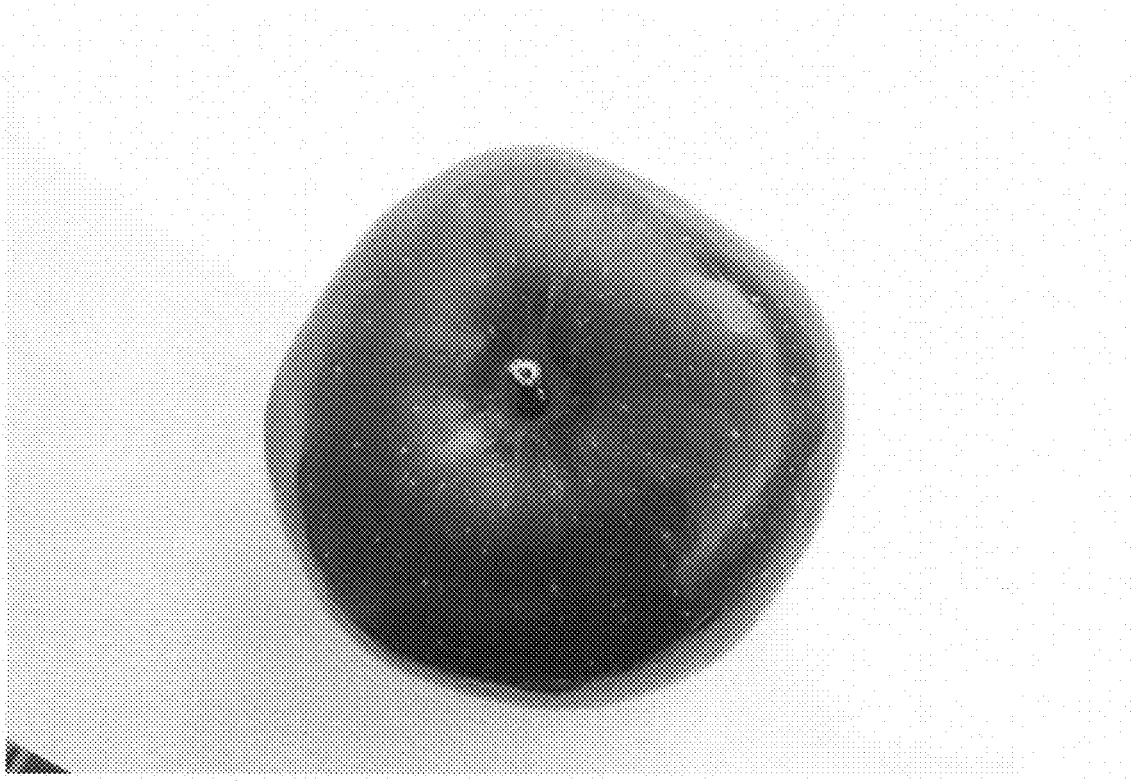

Fruit: Quantity per cluster, 1 to 3; size, large; diameter (average of 50 typical fruits), 85 mm; weight, 272 g; ratio height/width, 1.09; general shape in profile, elongated truncate-conical (FIG. 7); the maximum diameter is in medium-high position; ribbing is present; pronounced crowning at calyx end; depth of calyx eye, 11 mm; width of calyx end, 8 mm; depth of calyx end eye, 10 mm; width of calyx end eye, 23 mm (FIG. 8); depth of stalk cavity, 15 mm; width of stalk cavity, 31 mm; length of stalk, 22 mm; thickness of stalk, 2.7 mm; colour of stalk, Greyed-Orange RHS 176A (FIG. 9); partially open sepals, (FIG. 8) length of sepals, 3.5 mm. FIG. 4 shows a typical 'Stark Gugger' apple at picking time.

Figure 10:
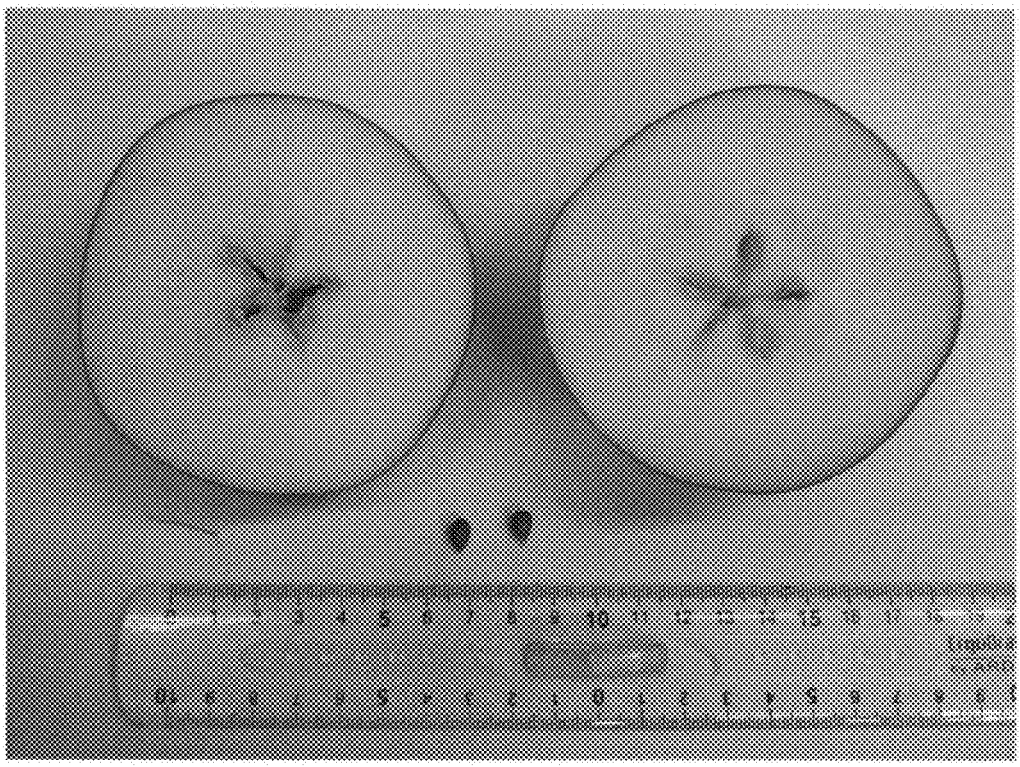
FIG. 10 illustrates the flesh of 'Stark Gugger' on the equatorial section and the seeds.

Fruit skin: Background colour, Red RHS 47A; over-colour, Purple-Red RHS N77A; amount of over-colour, 95 to 100% coverage; intensity of over-colour, dark purple; pattern of over-colour, solid flush without stripes (FIG. 7); thickness, thin to medium with purple colour penetrating in the first flesh cell layers (FIG. 10); bloom of skin, wax is present; greasiness of skin, absent; russet around stalk cavity, absent or very weak; russet around the calix eye, absent or very weak; number of cheeks per square cm, 5 to 6; shape of cheeks, round; size of cheeks, 0.7 mm; colour of cheeks, Greyed-White RHS 156D; russet around cheeks, absent.

Fruit flesh: Firmness, medium to firm; texture, medium to fine; colour, Yellow RHS 4D (FIG. 10); flavour, sweet; at harvest time 12-12.5 Brix and 3-3.5% acidity; aroma, good and intense aroma classical of the original 'Starking Delicious'; juiciness, moderately-juicy.

Fruit core: Vascular bundles evident; five partially open locules; usually 1 to 2 seeds per locule, shape of seed, oval elongated; colour of seeds, Greyed-Orange RHS 176A.

Fruit picking time: In 2012 at Bressanone area in Bolzano Province, Italy, the picking of 'Stark Gugger' began the 13$^{th}$ of September, (14 days earlier than 'Golden Delicious'). The high and early coloration allow for harvesting this variety in one picking. Table 1, below, reports apple maturation analysis of 12 fruits for each variety at two times. 'Stark Gugger' and 'Jeromine' were cultivated in the same field with the same growing conditions. At both times 'Stark Gugger' shows anticipated starch degradation (in the scale 1 is minimum, 5 is maximum starch hydrolysis) and anticipated sugar accumulation compared to Jeromine.

TABLE 1

Apple maturation analysis.

| Date | Location | Variety | Starch content (1 to 5 scale) | Sugar (Brix) | Firmness (kg/cm2) | Acidity (g/l) |
|---|---|---|---|---|---|---|
| Aug. 9, 2012 | Gugger Farm, Bressanone (BZ) | 'Stark Gugger' | 1.81 | 11.4 | 8.05 | 3.6 |
| Aug. 9, 2012 | Gugger Farm, Bressanone (BZ) | 'Jeromine' | 1.5 | 10.2 | 7.73 | 3.2 |
| Dec. 9, 2012 | Gugger Farm, Bressanone (BZ) | 'Stark Gugger' | 2.12 | 12.9 | 6.94 | 2.9 |
| Dec. 9, 2012 | Gugger Farm, Bressanone (BZ) | 'Jeromine' | 1.75 | 10.3 | 7.73 | 2.9 |

What is claimed is:

1. A new and distinct tree of *Malus domestica* Borkh named 'Stark Gugger', substantially as illustrated and described herein.

* * * * *